(12) United States Patent
Wei et al.

(10) Patent No.: US 11,135,592 B2
(45) Date of Patent: Oct. 5, 2021

(54) MULTIPLEX SLIDE PLATE DEVICE HAVING STORAGE TANK

(71) Applicant: Quark Biosciences Taiwan, Inc., Hsinchu County (TW)

(72) Inventors: Cheng-Wey Wei, Hsinchu County (TW); Chia-Hao Chang, Hsinchu County (TW)

(73) Assignee: Quark Biosciences Taiwan, Inc., Hsinchu County (TW)

( * ) Notice: Subject to any disclaimer, the term of this patent is extended or adjusted under 35 U.S.C. 154(b) by 117 days.

(21) Appl. No.: 16/233,121

(22) Filed: Dec. 27, 2018

(65) Prior Publication Data

US 2019/0126271 A1 May 2, 2019

Related U.S. Application Data

(63) Continuation-in-part of application No. 15/149,185, filed on May 9, 2016, now Pat. No. 10,415,084.
(Continued)

(30) Foreign Application Priority Data

Mar. 1, 2016 (TW) ................................. 105106095
Aug. 8, 2018 (TW) ................................. 107127589

(51) Int. Cl.
*B01L 3/00* (2006.01)
*C12Q 1/686* (2018.01)

(52) U.S. Cl.
CPC ..... *B01L 3/50851* (2013.01); *B01L 3/502715* (2013.01); *C12Q 1/686* (2013.01);
(Continued)

(58) Field of Classification Search
None
See application file for complete search history.

(56) References Cited

U.S. PATENT DOCUMENTS 9,709,469 B2 7/2017 Zhong et al.
2009/0246782 A1* 10/2009 Kelso ................ B01L 3/502761
435/6.16
(Continued)

FOREIGN PATENT DOCUMENTS

CN 101896275 11/2010
CN 105277725 1/2016
(Continued)

OTHER PUBLICATIONS

Liou, Modular component design for portable microfluidic devices, Microfluid Nanofluid, 10:465-474, 2011. (Year: 2011).*
(Continued)

*Primary Examiner* — Samuel C Woolwine
*Assistant Examiner* — Carolyn L Greene
(74) *Attorney, Agent, or Firm* — JCIPRNET

(57) ABSTRACT

A multiplex slide plate device is provided, including a slide plate, a sacrificial layer, and a housing. The slide plate has reaction vessels arranged in an array. The sacrificial layer has a microfluidic channel, which has an injection channel, a main channel, and a distal channel connected to each other. The housing is used to accommodate the slide plate and the sacrificial layer, and is composed of a cover and a tray, and the cover has an injection hole, an exhaust hole, and a storage tank. A sample solution and an oil are injected from the injection hole into the injection channel, wherein the sample solution is pushed by the oil. The sample solution loads into each of the reaction vessels while flowing through the main channel. Excess waste liquid flows from the exhaust hole into the storage tank, and is covered by the oil and cannot reflow.

8 Claims, 6 Drawing Sheets

Related U.S. Application Data which is a continuation-in-part of application No. 13/928,396, filed on Jun. 27, 2013, now Pat. No. 9,724,692.

(52) U.S. Cl.
CPC . *B01L 2200/027* (2013.01); *B01L 2300/0829* (2013.01); *B01L 2300/1805* (2013.01)

(56) References Cited

U.S. PATENT DOCUMENTS

| | | | | |
|---|---|---|---|---|
| 2011/0053289 A1* | 3/2011 | Lowe | ............... | G01N 33/558 436/501 |
| 2012/0067723 A1* | 3/2012 | Rearick | ............ | G01N 27/4145 204/408 |

FOREIGN PATENT DOCUMENTS

| | | | | |
|---|---|---|---|---|
| TW | I411779 | | 10/2013 | |
| TW | I421495 | | 1/2014 | |
| WO | WO-2008060604 A2 * | 5/2008 | ....... | C12Q 2565/629 |

OTHER PUBLICATIONS

Yuejun Kang1 et al., "Continuous particle separation with localized AC-dielectrophoresis using embedded electrodes and an insulating hurdle", Electrochimica Acta, vol. 54, issue 6, Feb. 15, 2009, pp. 1715-1720.

Somenath Roy et al.,"A microfluidic-assisted microarray for ultrasensitive detection of miRNA under an optical microscope",Lab Chip, 11(11),Jun. 7, 2011, pp. 1886-1894.

Daniel C. Leslie et al., "Platinum nanoparticle-facilitated reflective surfaces for non-contact temperature control in microfluidic devices for PCR amplification",Lab Chip,12(1), Jan. 7, 2012, pp. 127-132.

Ayse Rezzan Kose et al., "Ferrofluid mediated nanocytometry",Lab Chip,12(1), Jan. 7, 2012, pp. 190-196.

Mohamed Lemine Youba Diakite et al., "A low-cost, label-free DNA detection method in lab-on-chip format based on electrohydrodynamic instabilities, with application to long-range PCR",Lab Chip,12(22), Nov. 21, 2012, pp. 4738-4747.

Sandeep Kumar Jha et al., "An integrated PCR microfluidic chip incorporating aseptic electrochemical cell lysis and capillary electrophoresis amperometric DNA detection for rapid and quantitative genetic analysis",Lab Chip, 12(21),Nov. 7, 2012, pp. 4455-4464.

* cited by examiner

_US 11,135,592 B2_

MULTIPLEX SLIDE PLATE DEVICE HAVING STORAGE TANK

CROSS-REFERENCE TO RELATED APPLICATIONS

This application is a continuation-in-part application of and claims the priority benefit of U.S. patent application Ser. No. 15/149,185, filed on May 9, 2016, now pending. The prior U.S. patent application Ser. No. 15/149,185 is a continuation-in-part application of and claims the priority benefit of U.S. patent application Ser. No. 13/928,396, filed on Jun. 27, 2013, now patented. The prior U.S. patent application Ser. No. 15/149,185 also claims the priority benefit of Taiwan Patent Application No. 105106095, filed on Mar. 1, 2016. This application also claims the priority benefit of Taiwan Patent Application No. 107127589, filed on Aug. 8, 2018. The entirety of each of the above-mentioned patent applications is hereby incorporated by reference herein and made a part of this specification.

BACKGROUND OF THE INVENTION

Field of the Invention

The invention relates to a multiplex slide plate device for molecular biological detection, and more particularly, to a multiplex slide plate device for a polymerase chain reaction (PCR) having a storage tank for storing waste liquid.

Description of Related Art

In the field of molecular biological detection, it is usually required to perform tests of multiple items and targets for a sample. For example, measuring several single-nucleotide polymorphism (SNP) genotypes, or a number of gene expression levels of a sample via polymerase chain reaction (PCR) assays. At this time, it is required to compose multiple DNA or RNA assays into a test panel. At least two specific DNA primer molecules are included in each set of test reagents in the PCR test (for some PCR assays, additional target-specific reporter probes are included), and this pair of primers has to correctly mix with the DNA template extracted from the sample to be tested, so as to measure the presence or the amount of the specific DNA targets in the sample.

Traditionally, the pair of primers and the sample are disposed in the same reaction vessel for PCR. The delivery is usually done by manually pipetting the solution from each vial which stores primer pairs, enzymes, dNTP mixture and buffer reagents and pipetting the sample via pipette to the reaction vessel. The most common vessel format is the 96-well plate. By the aforementioned delivery method, a PCR assay requires at least two pipetting operations, one for adding the sample and another one for adding the primer pairs to the reaction vessel. For example, when using a test kit to detect 36 targets in a sample, it needs at least 36 pipettings to add each pair of primers to 36 different reaction vessels, and another 36 pipettings to add the sample to each of the above reaction vessels. This kind of operation method is not only complicated and error-prone, but also labor-intensive.

If the primer pairs are pre-filled in each of the reaction vessels, the experiment operator only needs to add sample to the pre-filled vessels. As for the above-mentioned example of detecting 36 targets in one sample, it requires only 36 pipettings for adding sample into 36 pre-filled reaction vessels. Besides, the reaction vessel volume can be reduced simultaneously to nano-liter range, so as to save the amount of reaction reagents. As a result, the format of 96-well plate, which is a common carrier vessel, is changed into a slide-like micro-titter plate by this improvement.

However, the size and volume of reaction vessels (also called micro-wells or nano-wells) in a micro-titer plate are too small to be filled with the primer pairs or samples manually without causing cross-contamination between neighbouring vessels (i.e. the primer pairs escape from one well to other wells). Therefore, special microfluidic dispensing technology is required. In more detail, primer pairs are delivered to each of the nano-wells in advance and immobilized onto the inter-surfaces of the nano-well. Afterwards, the user may add the sample into each of the reaction vessels by single pipetting operation or single microfluidic channel without worrying about primers escaping from one well to other wells, such that the cross-contamination between wells is minimized.

When the sample testing is performed subsequently, each reaction vessel must be filled with the predetermined amount of sample. The traditional method is to use pipette or needle dispensers to load the sample "one by one" into the reaction wells. However, as the volume of reaction vessel becomes smaller and the inter-well distance becomes smaller, special mechanical structure dispenser or paths may be needed to reach each reaction vessel individually, which is complicated and time-consuming. If adding sample into each of the reaction vessels by single pipetting or single microfluidic channel is achieved by a special slide plate device, it is possible to greatly simplify the manual operation required in PCR reagent preparation, and enhance the convenience when sample filling.

SUMMARY OF THE INVENTION

The invention provides a multiplex slide plate device. The multiplex slide plate device of the invention is for molecular biological detection, more specifically, for PCR, and even more specifically, for real-time PCR. The sample can be loaded into each reaction vessel of the slide plate quickly and uniformly through the multiplex slide plate device of the invention, and all of the reaction vessels can be filled in an extremely short time by single pipetting. In addition, excess waste liquid can be stored in the storage tank, and the storage tank further has a foolproof and positioning functions.

A multiplex slide plate device is provided, including a slide plate, a sacrificial layer, and a housing. The slide plate has a plurality of reaction vessels, a first injection hole, and a first exhaust hole, wherein the reaction vessels are arranged in an array, and each of the reaction vessels has an opening portion and a bottom portion. The sacrificial layer has a microfluidic channel, wherein the microfluidic channel has an injection channel, a main channel, and a distal channel connected to each other, the sacrificial layer is assembled to the slide plate, and the main channel is assembled facing the opening portion. The housing is used to accommodate the slide plate and the sacrificial layer and is composed of a cover and a tray, wherein the cover is assembled to the tray, and the cover has a second injection hole, a second exhaust hole, and a storage tank. The sample solution and the oil are sequentially injected from the second injection hole and the first injection hole into the injection channel, and the sample solution is pushed using the oil, such that the sample solution and the oil flow from the injection channel to the distal channel through the main channel. The sample solution loads into each of the reaction vessels while flowing through the main channel. The oil removes the sample solution not loaded in the reaction vessels while flowing through the main channel. Excess waste liquid flows from the distal channel through the first exhaust hole and the second exhaust hole into the storage tank, and is covered by oil and cannot reflow.

In an embodiment of the invention, the multiplex slide plate device further includes a panel member assembled to the cover and covering the storage tank, and having a label or a different exterior color for identifications of different test samples, targets, or functions.

In an embodiment of the invention, the multiplex slide plate device further includes a capping member assembled to the cover and the panel member, wherein after the sample solution and the oil are sequentially injected from the second injection hole and the first injection hole, the second injection hole is covered using the capping member to prevent the sample solution and the oil from splashing and preventing a biochemical reaction contamination.

In an embodiment of the invention, the material of the housing includes a thermally conductive material.

In an embodiment of the invention, the tray has a groove to accommodate the slide plate and the sacrificial layer.

In an embodiment of the invention, the material of the slide plate includes a transparent material.

In an embodiment of the invention, the transparent material includes polycarbonate.

In an embodiment of the invention, the material of the sacrificial layer includes wax.

In an embodiment of the invention, the oil includes mineral oil or silicone oil.

In an embodiment of the invention, during the experiment of the polymerase chain reaction, heating is performed to melt the sacrificial layer, and the melted sacrificial layer is mixed with the oil.

Based on the above, the invention provides a multiplex slide plate device having a storage tank, which allows the sample to quickly and uniformly load into each of the reaction vessels of the slide plate while flowing through the main channel of the sacrificial layer, and then the sample solution not loaded into the reaction vessels is removed by the oil. As a result, all of the reaction vessels may be filled in an extremely short time by single pipetting, thus simplifying the experiment operation and saving time. In addition, excess waste liquid can flow from the distal channel through the first exhaust hole and the second exhaust hole into the storage tank, and covered by the oil, such that the excess waste liquid cannot reflow. Therefore, no additional steps are required to remove the waste liquid, which is more convenient and time-saving in operation. At the same time, the storage tank further has foolproof and positioning functions.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

The invention provides a multiplex slide plate device that may be widely applied to different types of reaction assays. In the following, the terms used in the specification are defined first.

A reagent may refer to a formulation of several ingredients used for a particular test/detection. For example, in the test using polymerase chain reaction (PCR), the testing reagent includes a pair of primers, enzymes, dNTPs, fluorescent reporters, salts and etc. During application, the different primer pairs and fluorescent reporters may be added into the reaction vessel firstly, and then followed by mixing the enzymes, dNTP, and other additives with the sample into the reaction vessel.

Sample(s) generally refers to the nucleic acid sample being tested. For example, the sample may be nucleic acid fragments (including DNAs or RNAs) extracted from sources including blood, tissue or saliva.

Assay(s) or test(s) may refer to one or more assays or test items performed to the same sample. For example, using PCR to detect a nucleic acid sample for 300 SNP genotype, such detection includes a number of PCR test items by checking each genotype (A, T, C, G) of each SNP. For example, using real time PCR to determine the nucleic acid amount of a specific sequence.

Sample solution refers to the mixture or mixing solution of the aforementioned sample and master mix.

Reaction vessel may represent each tube or reaction tube of the tube plate, the hole(s) or well(s) in the micro-titer plate, the reaction well(s) or pit(s) in the test slide plate or the array plate. As described herein, the "slide plate", "slide piece", "assay array plate" or "assay plate" may refer to the same substrate or plate accommodating the aforementioned reaction vessels.

When the liquid volume in the vessels is reduced to a certain level, the liquid flow in the vessel is mainly dominated by surface adhesion, rather than gravity. If the liquid volume in the vessel is only a few nano-liters, the liquid has higher surface adhesion to the vessel (nanowell), so that the liquid may be regarded as stable as an adhesive attached to the bottom or the wall of the vessel.

Preferably, the reaction vessel may be individual reaction well(s) or pit(s) in the test slide or the assay array plate. As discussed above, it is preferable to utilize the reaction vessel of a smaller volume, ranging from several to hundreds of nano-liters, for example.

Figure 1:
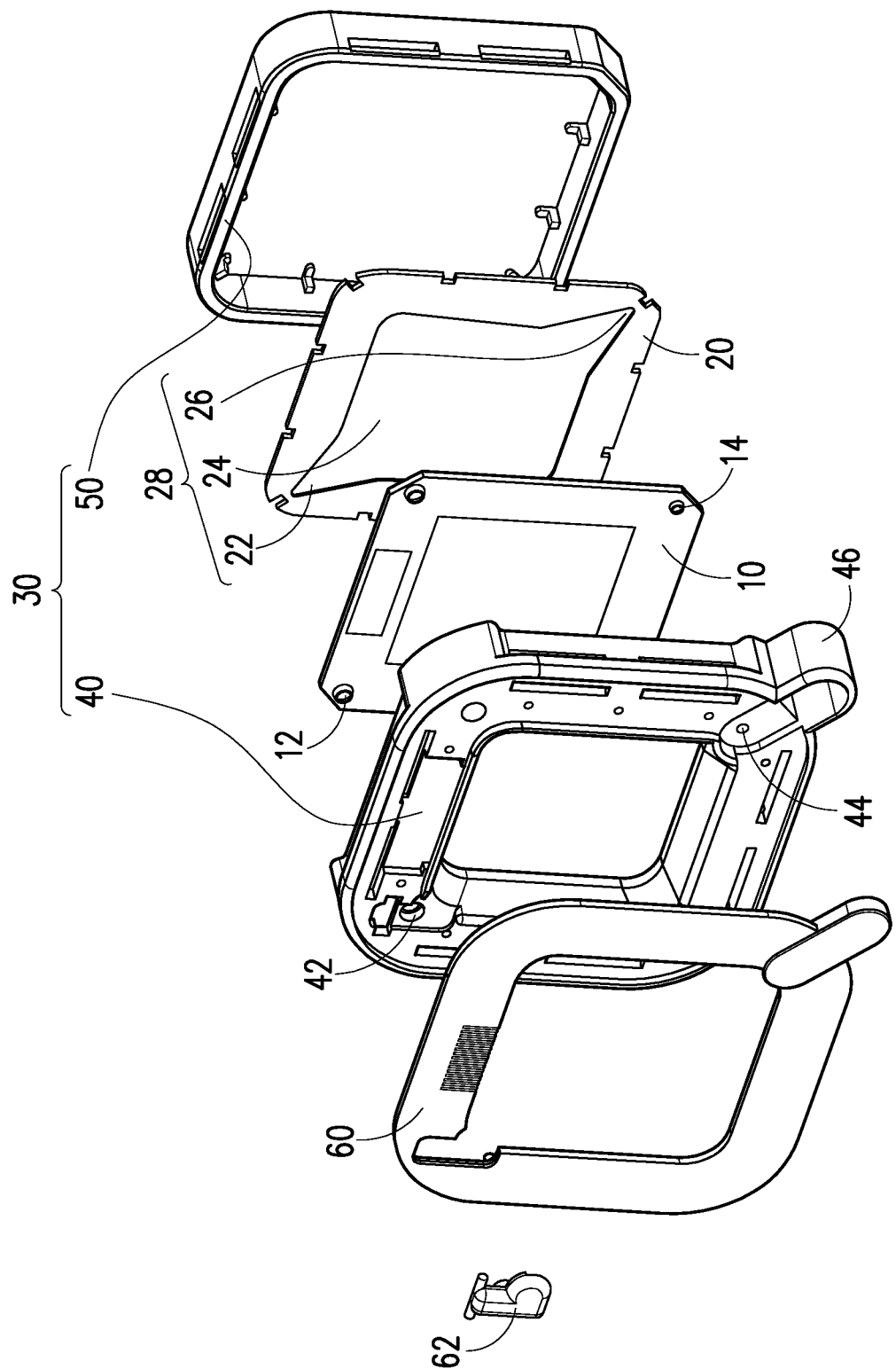
FIG. 1 is a schematic view illustrating the structure of a multiplex slide plate device according to an embodiment of the invention.

FIG. 1 is a schematic view illustrating the structure of a multiplex slide plate device according to an embodiment of the invention.

Referring to FIG. 1, a multiplex slide plate device includes a slide plate 10, a sacrificial layer 20, a housing 30, a panel member 60, and a capping member 62, wherein the housing 30 may be used to accommodate the slide plate 10 and the sacrificial layer 20. The structure of the slide plate 10 in FIG. 2 and FIG. 3 is illustrated in the following description.

Figure 2:
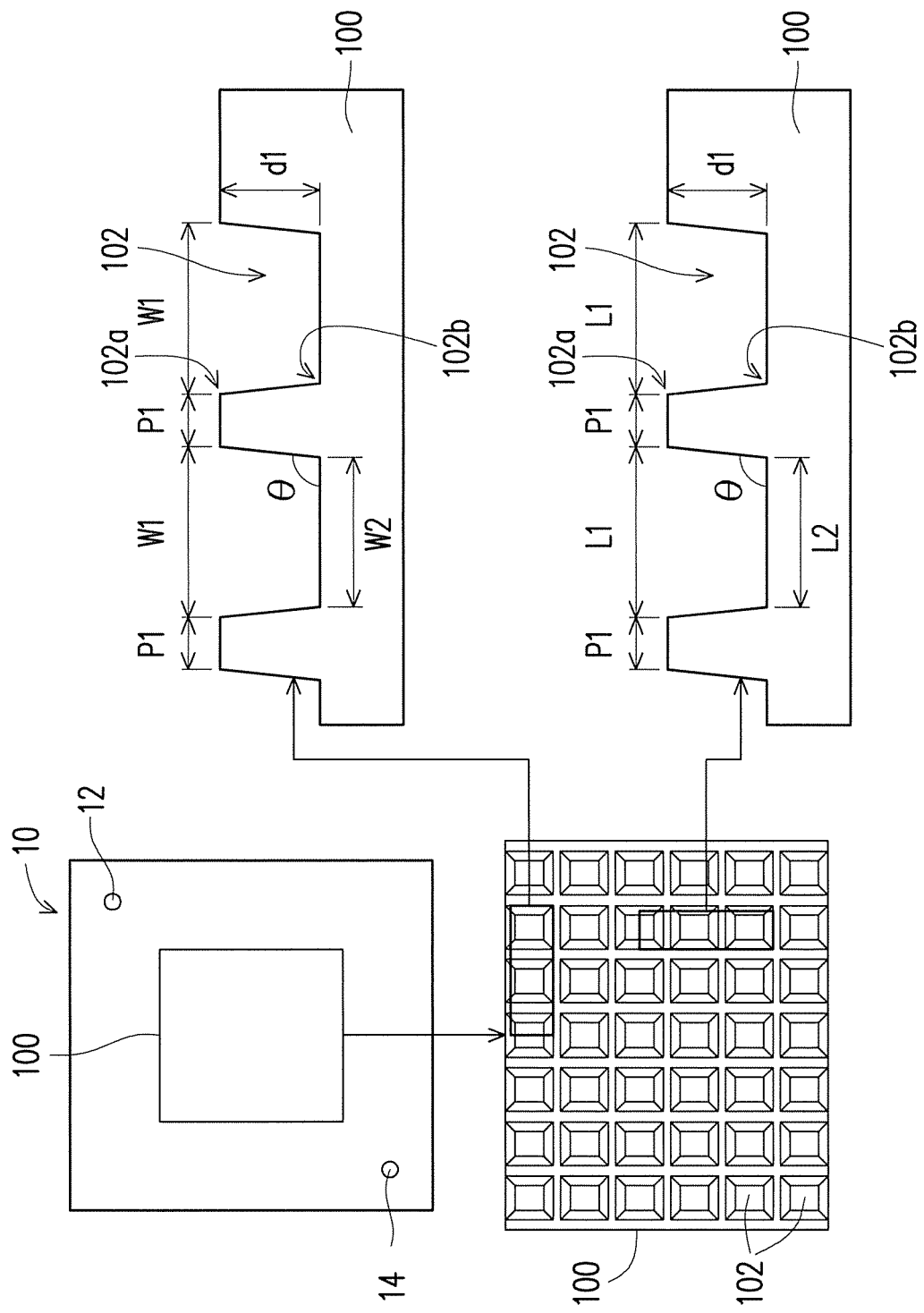
FIG. 2 is a schematic view illustrating the structure of a slide plate according to an embodiment of the invention.
Figure 3:
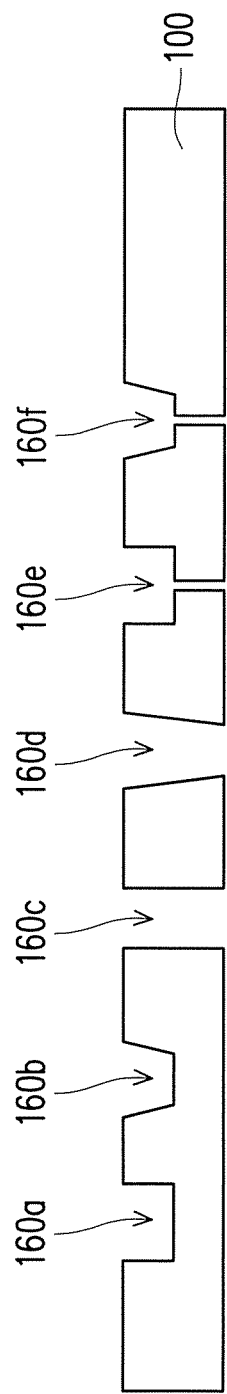
FIG. 3 is a schematic cross-sectional view of reaction vessels of a slide plate according to an embodiment of the invention.

FIG. 2 is a schematic view illustrating the structure of a slide plate according to an embodiment of the invention.

Referring to FIG. 2, the slide plate 10 has an assay region 100, and the area of the assay region 100 is 22.5 mm×22.5 mm. The assay region 100 includes a plurality of reaction vessels 102, wherein the reaction vessels 102 are arranged in an n×n array. Besides, the slide plate 10 further includes an injection hole 12 and an exhaust hole 14. In the present embodiment, the overall dimension of the slide plate 10 is 36 mm×36 mm×0.8 mm, for example. More specifically, the material of the slide plate 10 may include a transparent material, and the transparent material may be polycarbonate (PC), for example, but the invention is not limited thereto.

Referring to FIG. 2, from the cross-sectional views (right part of FIG. 2) of the slide plate 10, each of the reaction vessels 102 may be wide in the opening portion 102a and narrower in the bottom portion 102b. In the present embodiment, each of the reaction vessels 102 has a depth of 200 μm (d1), with 410 μm (L1)×410 μm (W1) for the dimension of the opening portion 102a, and 220 μm (L2)×220 μm (W2) for the dimension of the bottom portion 102b, for example. The pitch (P1) between the reaction vessels 102 may range from 27 m~45 μm. The slanted sidewall of the reaction vessels 102 may have an angle θ from 90 to 180 degrees, preferably from 110 to 160 degrees, more preferably from 120 to 140 degrees, for example. Each of the reaction vessels 102 may accommodate 21.65 nano-liters of sample solution, for example.

FIG. 3 is a schematic cross-sectional view of reaction vessels of a slide plate according to an embodiment of the invention.

Referring to FIG. 3, the reaction vessels of the slide plate 10 may be designed with different shapes or arrangement. For example, the reaction vessels 160a and 160b are concave cavities formed within the slide plate 10 but not penetrating through the slide plate 10. The reaction vessels 160b, 160d and 160f have slanted sidewalls. The reaction vessels 160c, 160d, 160e and 160f penetrate through the slide plate 10 and have two open ends at the top and bottom surfaces of the slide plate 10. Due to the capillary phenomenon, the sample liquid is steadily held in the reaction vessels 160c, 160d, 160e and 160f. The reaction vessel 160d penetrates through the slide plate 10 and has two open ends at the top and bottom surfaces of the slide plate 10, and has slanted sidewalls connecting the two open ends.

However, the structures in FIG. 2 and FIG. 3 are for illustration only, and the shape, size or number of the reaction vessels of the invention is not limited. The cross-sectional shape of the reaction vessels may be a circle, square or polygon, for example.

Generally, as the primers are soluble in aqueous solvents or solutions, the slide plate of the invention may be designed to be hydrophilic in the inner wall and the bottom surface of the reaction vessels, and to be hydrophobic in the regions between the reaction vessels. The reagent(s) or probe(s) will be attached only to the hydrophilic regions, that is, the inner wall and the bottom surface of the reaction vessels. The size of each reaction vessel may be less than 1 mm. In this scale, small amounts of sample fluid may overflow large numbers of reaction vessels in 10 seconds, so as to improve sample loading efficiency significantly.

Referring to FIG. 1, the sacrificial layer 20 has a microfluidic channel 28, wherein the microfluidic channel 28 has an injection channel 22, a main channel 24 and a distal channel 26 connected to each other. In the present embodiment, the material of the sacrificial layer 20 may include wax, so the sacrificial layer 20 melts when it is heated to about 60° C. in PCR. However, the invention is not limited thereto, and any material with a melting temperature range of more than room temperature to 60° C. may also be used, and the material with a melting temperature of about 60° C. is preferred. More specifically, the dimension of the sacrificial layer 20 is 38 mm×38 mm×0.6 mm, for example. The depth of the microfluidic channel 28 is 0.2 mm, for example. The dimension of the main channel 24 is 33 mm×33 mm, for example. Referring to FIG. 1 and FIG. 2, the sacrificial layer 20 is assembled to the slide plate 10, wherein the main channel 24 faces the opening portion 102a of the reaction vessels 102 in the slide plate 10.

As shown in FIG. 1, the housing 30 may be composed of a cover 40 and a tray 50, wherein the cover 40 is assembled to the tray 50, and the tray 50 may have a groove accommodating the slide plate 10 and the sacrificial layer 20. More specifically, the dimension of the cover 40 is 50 mm×50 mm×8 mm, for example. The dimension of the tray 50 is 42 mm×42 mm×4.4 mm, for example. The cover 40 has an injection hole 42, an exhaust hole 44, and a storage tank 46. The storage tank 46 has the functions of waste liquid storage and foolproof positioning. Since the storage tank 46 has a convex structure, the multiplex slide plate device of the invention may be mounted on the machine without being upside down, thus achieving the effect of foolproof positioning.

In the present embodiment, the cover 40 and the tray 50 are combined with each other by latching. Such a combining method generates sufficient downward pressure to achieve a better sealing effect, so as to prevent the liquid from leaking. However, the invention is not limited thereto, and the cover 40 and the tray 50 can also be combined with each other via a glue or other fixing means. More specifically, the housing 30 has a thermally conductive effect in PCR. The material of the housing 30 may include a thermally conductive material, wherein the thermally conductive material may be metal such as aluminium or copper, graphite, or wafer, but the invention is not limited thereto. In addition, the housing 30 is able to isolate the slide plate 10 and the sacrificial layer 20 from the external environment, so as to prevent the reaction from being affected.

As shown in FIG. 1, the panel member 60 is assembled to the cover 40 and covers the storage tank 46, and the panel member 60 may have a label or different exterior colors for identification of different test samples, targets, or functions. More specifically, when the multiplex slide plate device of the invention is applied in an equipment (such as a thermal cycler) provided with a label-reading device, the label-reading device can read the label on the panel member 60 to identify different detection samples, wherein the label is, for example, a handwritten mark, a bar code, or other marks, but the invention is not limited thereto, and a suitable label can also be selected according to needs and the label-reading device used. In addition, an exterior color design can also be applied to the panel member 60 according to different operating requirements for identification of different detection targets or functions, such as the identification of different detection target (miRNA or mRNA detection) slide plates or the differentiation of slide plate devices with test samples and blank slide plate devices without test samples during mounting.

As shown in FIG. 1, the capping member 62 is assembled to the cover 40 and the panel member 60. During the operation, the capping member 62 may be opened first, and after the sample solution and the oil are sequentially injected from the injection hole 42 and the injection hole 12, the capping member 62 is closed. The injection hole 42 may be closed using the capping member 62 to prevent the sample solution and the oil from splashing and prevent a biochemical reaction contamination.

Figure 4:
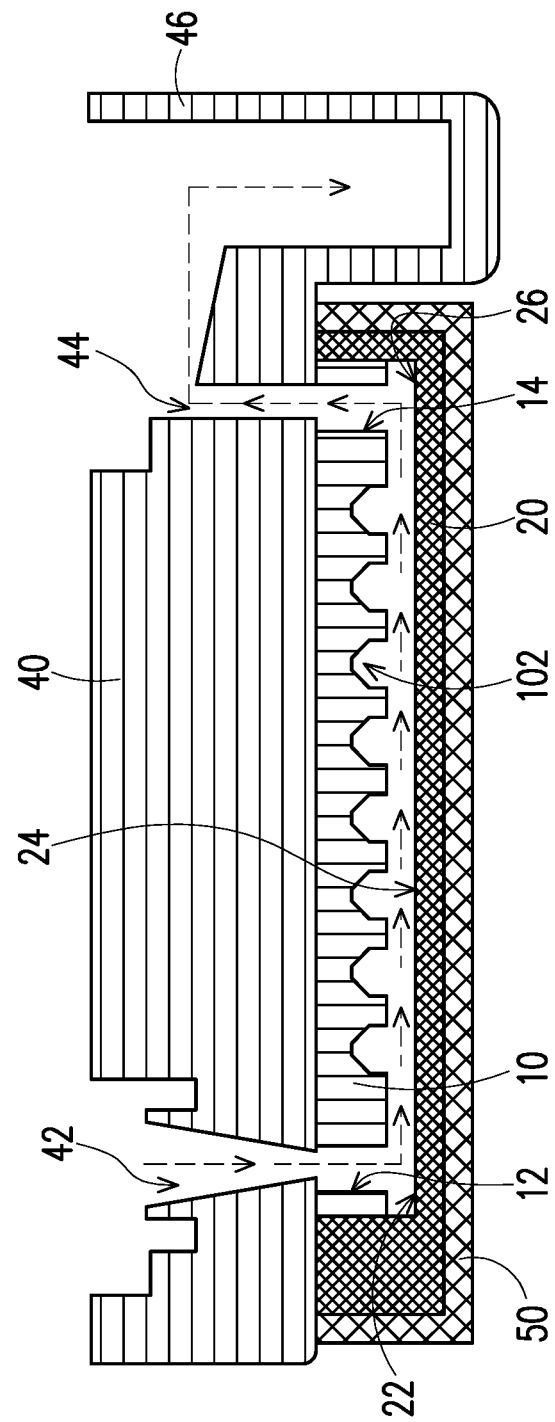
FIG. 4 is a schematic view illustrating a multiplex slide plate device applied in a sample solution loading according to an embodiment of the invention.
Figure 5A:
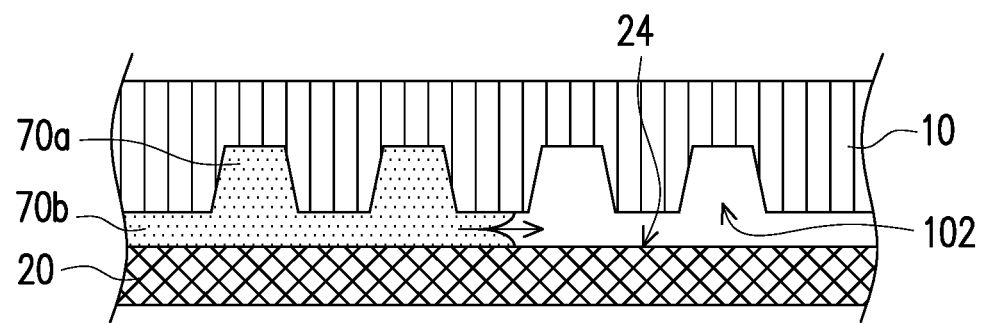
FIG. 5A to FIG. 5C are schematic views of an operating method of a multiplex slide plate device according to the invention.
Figure 5B:
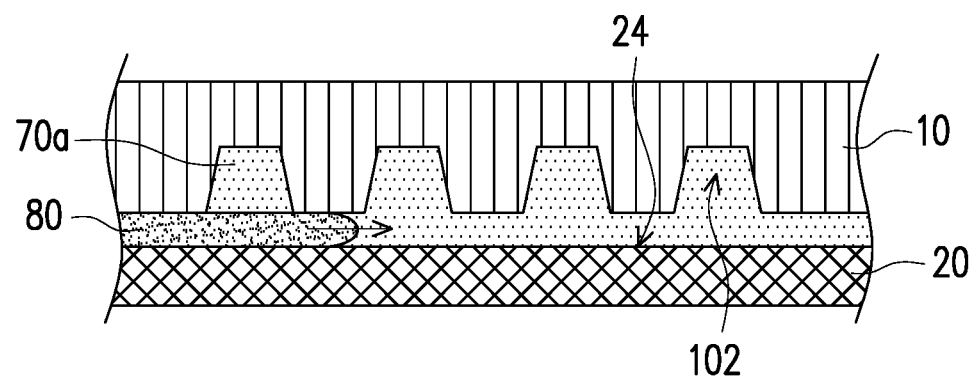
Figure 5C:
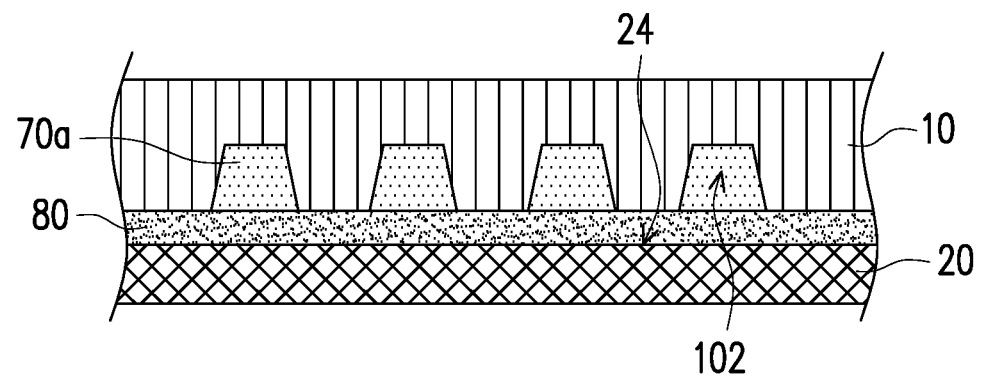
Figure 6A:
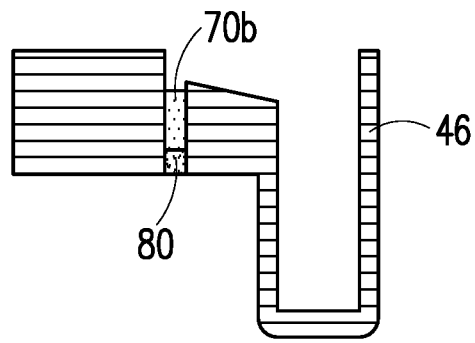
FIG. 6A to FIG. 6C are partial operational views of a storage tank of a multiplex slide plate device according to the invention.
Figure 6B:
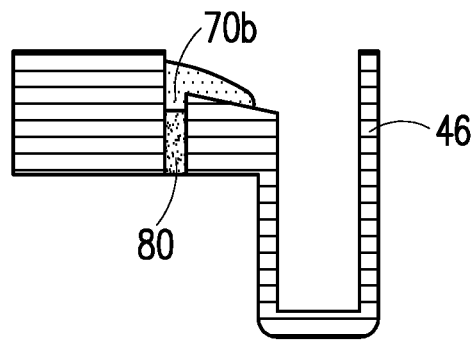
Figure 6C:
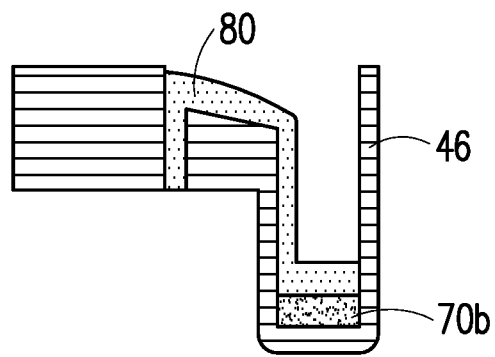

FIG. 4 is a schematic view illustrating a multiplex slide plate device applied in a sample solution loading according to an embodiment of the invention. FIG. 5A to FIG. 5C are schematic views of an operating method of a multiplex slide plate device according to the invention. FIG. 6A to FIG. 6C are partial operational views of a storage tank of a multiplex slide plate device according to the invention. Next, the structure of the multiplex slide plate device in an embodiment of the invention and its application in sample solution loading will be illustrated in the following descriptions by referring to FIG. 1, FIG. 4, FIG. 5A to FIG. 5C, and FIG. 6A to FIG. 6C.

As shown in FIG. 1 and FIG. 4, the capping member 62 may be opened first, and the sample solution and the oil may be sequentially injected from the injection hole 42 of the cover 40 and the injection hole 12 of the slide plate 10 into the injection channel 22 via pipetting or other suitable liquid dispensers. The sample solution is pushed by the oil, such that the sample solution and the oil flow from the injection channel 22 through the main channel 24 to the distal channel 26. More specifically, the total input amount of the sample solution is 60 μl, for example. The oil is mineral oil or silicone oil, for example.

Referring to FIG. 1, FIG. 4, and FIG. 5A simultaneously, the sample solutions 70a and 70b load into each of the reaction vessels 102 of the slide plate 10 while flowing through the main channel 24 (the flowing direction of the sample solutions is illustrated by the dashed arrow in FIG. 4). As shown in FIG. 1, FIG. 4, FIG. 5B, and FIG. 5C, the oil 80 removes the sample solution 70b which is not loaded into the reaction vessels 102 while flowing through the main channel 24 (the flowing direction of the oil 80 is illustrated by the dashed arrow in FIG. 4). As shown in FIG. 1, FIG. 4, and FIG. 6A to FIG. 6C, excess waste liquid such as the sample solution 70b not loaded into the reaction vessels 102 flows from the distal channel 26 through the exhaust hole 14 and the exhaust hole 44 and into the storage tank 46, and is covered by the oil 80 and cannot reflow.

In FIG. 1, the injection hole 42 and the exhaust hole 44 of the cover 40 and the injection hole 12 and the exhaust hole 14 of the slide plate 10 are respectively arranged in a diagonal line, but the invention is not limited thereto. In other words, the arrangement of the injection hole 12 and the exhaust hole 14 may be adjusted according to the arrangement of the injection channel 22 and the distal channel 26 of the sacrificial layer 20, as long as the sample solution is fully extended in the flowing process. In addition, the arrangement of the injection hole 42 and the exhaust hole 44 of the cover 40 depends on the arrangement of the injection hole 12 and the exhaust hole 14 of the slide plate 10. Therefore, it may be adjusted according to the arrangement of the injection channel 22 and the distal channel 26 of the sacrificial layer 20.

Finally, in the PCR experiment process, the sacrificial layer is heated to melt, and the melted sacrificial layer mixes with the oil, wherein the melting temperature of the sacrificial layer may be about 60° C. It should be noted that the distance between the slide plate and the sacrificial layer of the invention is at least about 100 μm (for example, 100 μm to 400 μm), and the sacrificial layer has a certain thickness (for example, 200 μm to 500 μm). Therefore, when the melted sacrificial layer mixes with the oil, the distance between the slide plate and the tray is about 600 μm, so the reaction may be performed successfully. A certain distance between the slide plate and the tray may be maintained without adding an excess amount of sample, so it is able to save the input amount of sample.

Based on the above, the invention provides a multiplex slide plate device for molecular biological detection, which allows the sample solution to quickly and uniformly load into each of the reaction vessels of the slide plate while flowing through the main channel of the sacrificial layer, and then the sample solution not loaded into the reaction vessels is removed by the oil. As a result, all of the reaction vessels may be filled in an extremely short time with single pipetting, thus simplifying the experiment and saving time. In addition, a certain distance between the slide plate and the tray may be maintained without adding an excess amount of sample, so the invention is also able to save the input amount of sample. On the other hand, excess waste liquid may flow from the distal channel into the storage tank and be covered by the oil, such that the excess waste liquid cannot reflow. Therefore, no additional steps are required to remove the waste liquid, which is more convenient and time-saving in operation. At the same time, the storage tank further has foolproof and positioning functions.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A multiplex slide plate device, for a polymerase chain reaction, comprising:
   a slide plate having a plurality of reaction vessels, a first injection hole, and a first exhaust hole, wherein the reaction vessels are arranged in an array, and each of the reaction vessels has an opening portion and a bottom portion;
   a sacrificial layer having a microfluidic channel, wherein the microfluidic channel has an injection channel, a main channel, and a distal channel connected to each other, the sacrificial layer is assembled to the slide plate, and the main channel is assembled facing the opening portion; and
   a housing to accommodate the slide plate and the sacrificial layer, wherein the housing is composed of a cover and a tray, wherein the cover is assembled to the tray, and the cover has a second injection hole, a second exhaust hole, and a storage tank having a convex structure.

2. The multiplex slide plate device of claim 1, further comprising a panel member assembled to the cover and covering the storage tank, and the panel member has a label or a exterior color for identification of different test samples, targets, or functions.

3. The multiplex slide plate device of claim 2, further comprising a capping member assembled to the cover and the panel member.

4. The multiplex slide plate device of claim 1, wherein a material of the housing comprises a thermally conductive material.

5. The multiplex slide plate device of claim 1, wherein the tray has a groove to accommodate the slide plate and the sacrificial layer.

6. The multiplex slide plate device of claim 1, wherein a material of the slide plate comprises a transparent material.

7. The multiplex slide plate device of claim 6, wherein the transparent material comprises polycarbonate.

8. The multiplex slide plate device of claim 1, wherein a material of sacrificial layer comprises wax.

* * * * *